United States Patent [19]

Thominet

[11] 3,959,477
[45] May 25, 1976

[54] METHODS OF PROTECTION AGAINST EMESIS IN MAMMALS BY ADMINISTRATION OF A HETEROCYCLIC BENZAMIDE

[75] Inventor: Michel Leon Thominet, Paris, France

[73] Assignee: Societe d'Etudes Scientifiques et Industrielles de l'Ile-de-France, Paris, France

[22] Filed: Mar. 24, 1975

[21] Appl. No.: 561,253

Related U.S. Application Data

[60] Division of Ser. No. 382,251, July 24, 1973, Pat. No. 3,891,671, which is a continuation of Ser. No. 145,871, May 21, 1971, abandoned, which is a continuation-in-part of Ser. No. 845,523, July 28, 1969, abandoned.

[30] Foreign Application Priority Data

Aug. 1, 1968  France ............................ 68.161593
Oct. 29, 1968  France ............................ 68.171761

[52] U.S. Cl. ................................ 424/274; 424/267
[51] Int. Cl.² ........................................ A61K 31/445
[58] Field of Search ..................... 424/274, 267, 244

[56]  References Cited
UNITED STATES PATENTS
3,043,874  7/1962  De Wald et al. ............. 260/326.4 X Primary Examiner—Frederick E. Waddell
Attorney, Agent, or Firm—Frank M. Nolan

[57]  ABSTRACT

The heterocyclic benzamides of this invention are particularly effective for the treatment of emesis in mammals. For example, when they are administered to dogs in relatively small dosage, they afford 100% protection against vomiting. They are also non-toxic in dosages for effecting complete control of vomiting.

8 Claims, No Drawings

METHODS OF PROTECTION AGAINST EMESIS IN MAMMALS BY ADMINISTRATION OF A HETEROCYCLIC BENZAMIDE

This application is a division of the copending application Ser. No. 382,251, filed July 24, 1973 now U.S. Pat. No. 3,891,671. The application Ser. No. 382,251 is a continuation of the application Ser. No. 145,871, filed May 21, 1971, now abandoned. The application Ser. No. 145,871 is in turn a continuation-in-part of the application Ser. No. 845,523, filed July 28, 1969, now abandoned.

This invention relates to certain heterocyclic benzamides, their pharmaceutically acceptable acid addition salts and their quaternary ammonium salts. The invention also embraces methods of treating mammals afflicted with emesis.

The heterocyclic benzamides of this invention have the formula:

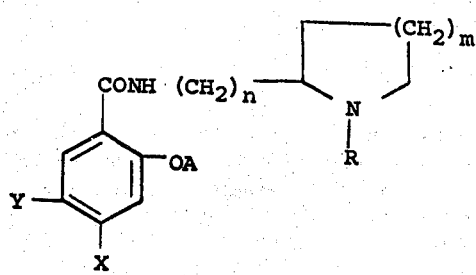

in which A is allyl or lower alkyl; R is allyl or lower alkyl; X is lower alkyl or hydroxy; Y is halogen, such as chlorine, bromine or fluorine; m is a whole number less than 3; and n is a whole number less than 4. Preferably, lower alkyl has less than 5 carbon atoms. Examples of lower alkyl are methyl, ethyl, propyl and isobutyl.

Throughout this disclosure, A, R, X, Y, m and n have the same meaning as heretofore defined.

When the compositions of this invention have one or more asymmetric carbon atoms, they may exist as the levo or dextro forms or racemic mixtures.

The compositions of this invention are useful as antiemetics and agents in alleviating behavoir disturbances and pain in mammals.

The heterocyclic benzamides of this invention are produced by reacting a heterocyclic amine having the formula:

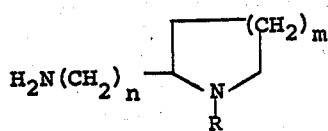

with an acid chloride or lower alkyl ester of a 2-alkoxy benzoic acid having the formula:

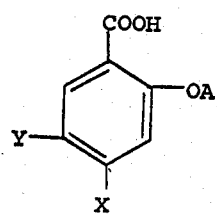

If the heterocyclic amine has one or more asymmetric carbon atoms, the levo, dextro or racemic mixture of such heterocyclic amine is employed to obtain the corresponding heterocyclic benzamide of this invention.

The acid addition salts of the heterocyclic benzamides of this invention are obtained by reacting the heterocyclic benzamide with the required acid. The acid may be an inorganic acid, for example, a mineral acid, such as hydrobromic acid, hydrochloric acid, sulfuric acid or phosphoric acid. The acid may also be an organic acid such as citric acid, tartaric acid, lactic acid or acetic acid.

The quaternary ammonium salts of the heterocyclic benzamides of this invention are produced by reacting the heterocyclic benzamides with an aliphatic or aromatic alkylating agent such as methyl chloride, methyl bromide, dimethyl sulfate or methyl p-toluene sulfonate.

The compounds of this invention may be administered in the form of ampules, tablets, drops, or in drinkable solutions containing pharmaceutically acceptable salts of a heterocyclic benzamide. The compounds of this invention with or without other compatible therapeutic ingredients, fillers or adjuvents may be conveniently administered in dosage unit forms. The daily dosage may vary over wide limits for the treatment of emesis, pain or behavior disturbances as determined by the veterinarian or physician. Desirably, the daily dosage may range from 50 to 500 $\mu$g/kg.

The compounds of the present invention are new and their pharmacological properties are significantly superior to those of the products disclosed in German Pat. No. 1,233,877 owned by the assignee of the present invention. Firstly, the compounds are chemically different. In the present invention, the X radical, in para of the benzamide function can be hydroxy or lower alkyl. In the compounds described in the German patent, on the other hand, the same radical may be: hydrogen, halogen, alkoxy, amino (or amino derivative). mercapto. sulfamido, acyl, but in no case hydroxy or lower alkyl. Moreover, the heterocycle which can be on the amide chain of the German patent is linked thereto by a nitrogen atom, for example:

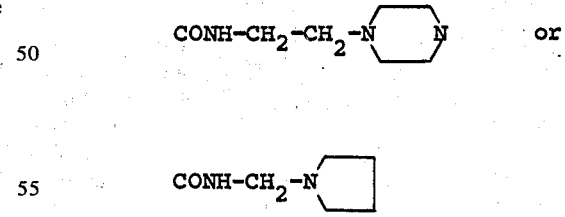

instead of being, as in the present invention, linked to the carbon atom placed in ortho of the nitrogen heteroatom.

Pharmacologically, the main difference is that for an equivalent, or superior, antiemetic property, the toxicities are much lower and the side effects much weaker, as shown by compounds having the following structures:

A 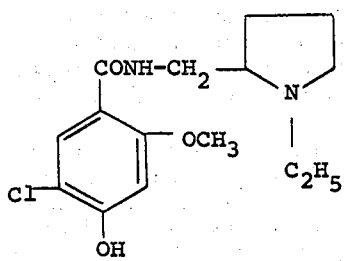

B 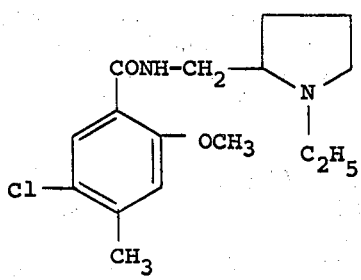

C 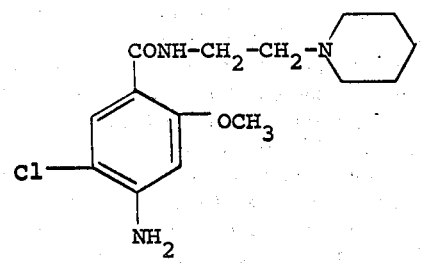

The LD₅₀ observed with the mouse and expressed in mg/kg for each of the compounds are:

A ⟶ 143–139
B ⟶ 29.5–28.6
C ⟶ 18.5–20.2

Compounds A and B are compounds of the present invention and are comparable with compound C of the German patent. The two heterocyclic chains carried by the amide of compounds A and B carry the same number of carbon atoms and the same heteroatom as that of the German patent. The compounds of the present invention, therefore, are significantly superior to those of German Pat. No. 1,223,877.

A more comprehensive understanding of this invention may be obtained from the following examples:

EXAMPLE I

N-(1-ETHYL-2-PYRRIDOLIDYLMETHYL)-2-METHOXY-4-METHYL-5-CHLOROBENZAMIDE

Stage A.

In a 1 liter flask, there are put 194 g (1 mole) of 2-chloro-5-acetoxytoluene and 150 g of anhydrous aluminum chloride. There is produced an active heating and a pasty mass forms. The mixture is brought to 120° C for 1½ hours. When cooled, 1 liter of warm water is added in small portions. It is acidified with hydrochloric acid and a yellow oil forms which is decanted and extracted in methylene chloride. The organic solution is washed with hydrochloric acid, diluted and dried in calcium chloride. The methylene chloride is removed under vacuum and the residue is distilled. There are obtained 173 g (yield 72%) of 2-hydroxy-4-methyl-5-chloroacetophenone.

Stage B. 2-Methoxy-4-methyl-5-chloroacetophenone

In a 2 liter flask equipped with an agitator, a refrigerant and a thermometer, there are put 153 g (0.82 mole) of 2-hydroxy-4-methyl-5-chloroacetophenone and 600 ml of acetone. The mixture is heated at 40° C and 103 g (0.82 mole) of dimethyl sulfate and 115 g of potassium carbonate are added. The mixture is refluxed for 2 hours and the acetone removed. The mixture is diluted with 1.500 liters of water. The 2-methoxy-4-methyl-5-chloroacetophenone formed crystallizes, is drained and washed with water. There are obtained 107 g (yield 64%) of product (m.p. 80°–81° C).

Stage C. 2-Methoxy-4-methyl-5-chlorobenzoic acid

In a 5 liter flask, there is put 450 ml of 30% soda and 1800 ml of water. It is cooled to 0° C and 118 g of chlorine are added to the mixture. Then the product obtained in Stage B is added in small portions. It is heated for 1 hour at 60° C. The mixture dissolves and then a precipitate comprising the sodium salt of the benzoic acid is formed. It is redissolved with heat in 3.500 liters of water. The solution is passed through animal charcoal and the 2-methoxy-4-methyl-5-chlorobenzoic acid formed by the addition of dilute hydrochloric acid is precipitated. The precipitate formed is drained, washed with water and dried. There are obtained 62 g (yield 69%) of product (m.p. 133°–134° C).

Stage D. 2-Methoxy-4-methyl-5-chlorobenzoyl chloride

In a 500 ml flask equipped with a refrigerant, there are introduced 87 g of thionyl chloride and about 31 g of 2-methoxy-4-methyl-5-chlorobenzoic acid and the mixture is heated on a water bath at 30° C. Dissolution occurs almost immediately, followed by reprecipitation. Then 31 g of acid is added. There is obtained a very thick, rose-colored precipitate. 41 g of thionyl chloride are added and the mixture is heated at 50°–55° C. At the end of ¾ of an hour at this temperature, if dissolution is not complete, heating is continued to dissolution (70°–75° C). The excess thionyl chloride is removed under vacuum. There are obtained 79 g (yield 99%) of 2-methoxy-4-methyl-5-chlorobenzoyl chloride (m.p. 106°–107° C).

Stage E.
N-(1-ethyl-2-pyrrolidylmethyl)-2-methoxy-4-methyl-5-chlorobenzamide

In a 1 liter flask equipped with an agitator, a thermometer and a dropping funnel, there are put 46 g (0.36 mole) of 1-ethyl-2-aminomethylpyrrolidine and 45 ml of methylethylketone. While maintaining the temperature of the mixture at about 5° C, there are added dropwise 79 g (0.36 mole) of 2-methoxy-4-methyl-5-chlorobenzoyl chloride dissolved in 400 ml of methylethylketone. The introduction requires about 1 hour. There is precipitation of N-(1-ethyl-2-pyrrolidylmethyl)-2-methoxy-4-methyl-5-chlorobenzamide hydrochloride which is drained, washed on a filter with methylethylketone and air-dried. There are obtained 114 g (yield 91%) of product in the form of white crystals (m.p. 162°–163° C).

EXAMPLE II

N-(1-ETHYL-2-PYRROLIDYLMETHYL)-2-METHOXY-4-HYDROXY-5-CHLOROBENZAMIDE

Stage A. Methyl 2-hydroxy-4-benzoyloxybenzoate

In a 3 liter flask equipped with an impervious agitator, a reflux refrigerant and a thermometer, there are introduced 251 g (1.5 mole) of methyl 2-4-dihydroxybenzoate and 1100 ml of acetone. To the solution obtained, 20 g of benzoyl chloride are added. It is heated at 40° C and 220 g of potassium carbonate are added slowly. There is a slight heating, the temperature rising to 52° C. Then 21 g of sodium iodide are added. It is then heated at reflux for 13½ hours. When the reaction is ended, 800 ml of acetone are distilled and the residue is recovered in 3.5 liters of water. The mineral salts dissolve and the benzoyl derivative precipitates. It is drained, washed with water and dried. There are obtained 382 g (yield 99%) of methyl 2-hydroxy-4-benzoyloxybenzoate (m.p. 103° C).

Stage B. Methyl 2-methoxy-4-benzoyloxybenzoate

In a 3 liter flask equipped with an impervious agitator, a reflux refrigerant and a thermometer, 299 g (1.2 mole) of methyl 2-hydroxy-4-benzoyloxybenzoate are dissolved in 800 ml of warm acetone and then 190 g of methyl sulfate, 192 g of potassium carbonate and 17 g of sodium iodide are added. It is heated at reflux until 0.2 ml of clear solution diluted in 2 ml of alcohol gives only a very faint coloration with a trace of ferric chloride or no coloration. The reaction lasts 4 hours.

It is then distilled in 600 ml of acetone and the residue recovered with 2 liters of water. The mineral salts dissolve and the methyl ester crystallizes. It is dried, washed with water and dried. There are obtained 283 g (yield 90%) of methyl 2-methoxy-4-benzoyloxybenzoate (m.p. 91° C).

Stage C. Methyl 2-methoxy-4-hydroxybenzoate

The product obtained in Stage B is hydrogenated in an autoclave in the presence of alcohol with Raney nickel as catalyst. The hydrogenation is done at 50° C and lasts 2½ hours. It is cooled, the nickel drained and the alcohol removed under vacuum. The methyl 2-methoxy-4-hydroxybenzoate formed crystallizes and is used for the following stage.

Stage D. Methyl 2-methoxy-4-hydroxy-5-chlorobenzoate

Into a 1 liter flask equipped with an agitator and thermometer, there are introduced 55 g (0.3 mole) of methyl 2-methoxy-4-hydroxybenzoate and 300 ml of acetic acid. It is heated at 60°–70° C until completely dissolved and cooled to 35° C. The ester recrystallized. Then 40 g of chlorosuccinimide are added in portions and then it is heated to 50°–55° C. It dissolves completely and the chlorinated ester crystallizes. The mixture is kept at 50°–55° C for 20 hours. There remains in solution only traces of the chlorosuccinimide. It is cooled, 3 liters of water added, drained, washed with water and dried. There are obtained 59 g (yield 90%) of methyl 2-methoxy-4-hydroxy-5-chlorobenzoate.

Stage E. N-(1-ethyl-2-pyrrolidylmethyl)-2-methoxy-4-hydroxy-5-chlorobenzamide

In a 500 ml flask with a 40 cm Vigreux column, there are put 57 g (0.25 mole) of methyl 2-methoxy-4-hydroxy-5-chlorobenzoate, 200 ml of xylene and 67 g (0.26 mole × 2) of 1-ethyl-2-aminomethylpyrrolidine. On dissolution, there is observed a slight recrystallization. The methyl alcohol produced which is in the form of an azeotrope with the xylene, is heated and slowly distilled at 64° C. 12 Ml of the azeotropic mixture is distilled in 1 hour and a small amount of the xylene is distilled in 1 more hour, at 130° C. In total, there is obtained 47 ml of distillate containing 9 ml of alcohol. The excess xylene and amine are then distilled under vacuum. There are obtained 139 g of a brown liquid. The product obtained is redissolved in 150 ml of warm water and acidified with 65 ml of concentrated hydrochloric acid. When cooled, the hydrochloride crystallizes. It is drained at 10°C and washed with 30 ml of ice water. There are obtained 80 g (yield 98%) of N-(1-ethyl-2-pyrrolidylmethyl)-2-methoxy-4-hydroxy-5-chlorobenzamide hydrochloride (m.p. 207°–208° C).

EXAMPLE III

DEXTRO N-(1-ETHYL-2-PYRROLIDYLMETHYL)-2-METHOXY-4-HYDROXY-5-CHLOROBENZAMIDE

Stages A through D are the same as described in Example II.

Stage E. In a 500 ml flask equipped with a 40 cm Vigreux column, there are put 40 g (0.184 mole) of methyl 2-methoxy-4-hydroxy-5-chlorobenzoate, 160 ml of xylene and 35.5 g of dextro 1-ethyl-2- aminomethylpyrrolidine. It is heated gently. There is complete dissolution when heating begins. The methyl alcohol formed as a methanol - xylene azeotrope is distilled at 61°–63° C. At the end of the reaction, a little xylene is distilled. In 90 minutes, 40 ml containing 7 ml of methyl alcohol are distilled. The excess xylene and amine are then distilled under vacuum. The residue is a solid. It is recovered with 300 ml of water, drained, washed until neutral as indicated by the phenolphthalein and dried at 60° C. There are obtained 58 g (yield 100%) of N-(1-ethyl-2-pyrrolidylmethyl)-4-hydroxy-5-chlorobenzamide in base state which are transformed to the hydrochloride. This is done by dissolving the base in 200 ml of absolute alcohol and adding an alcohol solution of 14.5 ml of concentrated hydrochloric acid in 40 ml of alcohol. The hydrochloride crystallizes, is drained, washed with alcohol, and air-dried. It is a white solid (m.p. 228° C; $[\alpha]_D = + 8°$ (5% water).

EXAMPLE IV

LEVO N-(1-ETHYL-2-PYRROLIDYLMETHYL)-2-METHOXY-4-HYDROXY-5-CHLOROBENZAMIDE

Stages A through D are the same as those described in Example II.

Stage E. In a 500 ml flask with a 40 cm Vigreux column, there are put 32 g (0.15 mole) of methyl 2-methoxy-4-hydroxy-5-chlorobenzoate, 120 ml of xylene and 23 g of levo 1-ethyl-2-aminomethylpyrrolidine. It is heated gently. A solution is obtained. The methyl alcohol formed in the form of a methanol-xylene azeotrope is distilled at 60°–62° C in about an hour. At the end of the reaction, 10 ml of xylene is distilled at 135° C. In the distillate, 5 ml of alcohol are recuperated for 6 ml theoretical.

The excess xylene and amine are then distilled under vacuum. The solid residue is recovered with 600 ml of water, drained, washed until neutral as indicated by phenolphthalein and dried at 45° C. This product is dissolved in 130 ml of absolute alcohol, after which 4.9 g of dry hydrochloric acid dissolved in 30 ml of alcohol + 4 ml of water are poured in. The levo N-(1-ethyl-2-pyrrolidylmethyl)-2-methoxy-4-hydroxy-5-chlorobenzamide formed crystallizes. It is drained and washed with alcohol. It is a white solid weighing 44 g (yield 89%) (m.p. 217°–220° C); $[\alpha]_D = -8°$ (5% water).

EXAMPLE V

N-(1-ETHYL-2-PYRROLIDYL-METHYL)-2-METHOXY-4-HYDROXY-5-CHLOROBENZAMIDE BROMOMETHYLATE 55 g (0.175 mole) of N-(1-ethyl-2-pyrrolidylmethyl)-2-methoxy-4-hydroxy-5-chlorobenzamide are dissolved by heating in 165 ml of absolute alcohol and the solution obtained is cooled. 18 G of methyl bromide are added and allowed to react for 84 hours. There is then found in the solution 0.158 mole of Br. Several gelatinous crystals are observed in suspension. All of the alcohol is then distilled. The residue obtained begins to crystallize at the end of three days. It is then recovered with 50 ml of absolute alcohol, dried, washed, and air-dried. A white solid is obtained, melting at 185°–186°C and composed of N-(1-ethyl-2-pyrrolidylmethyl)-2-methoxy-4-hydroxy-5-chlorobenzamide bromomethylate.

EXAMPLE VI

N-(1-ETHYL-2-PYRROLIDYLETHYL)-2-METHOXY-4-METHYL-5-CHLOROBENZAMIDE HYDROCHLORIDE

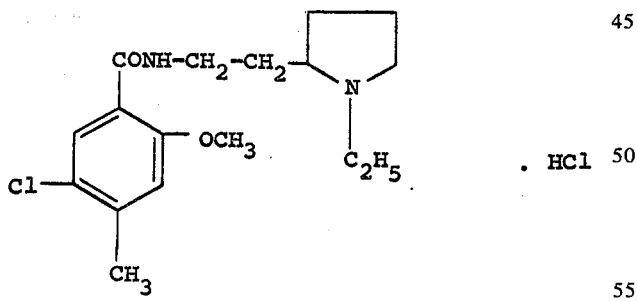

In a 500 ml flask equipped with an ascendant refrigerant and a thermometer, there are introduced 35.5 g of 2-methoxy-4-methyl-5-chlorobenzoic acid and 79 ml of thionyl chloride which are heated on a water bath at 30°C. Then a second fraction of 35.5 g of the same acid is added. The mixture is refluxed for one hour and the excess thionyl chloride is removed.

In a 1 liter flask equipped with a mechanical agitator, a thermometer and a dropping funnel, 51 g of N-ethyl-2-aminoethylpyrrolidine are dissolved in 60 ml of methylethylketone. It is cooled at 5°C and 77 g of 2-methoxy-4-methyl-5-chloro-benzoyl chloride dissolved in 400 ml of methylethylketone are added drop by drop, the temperature being maintained between 5° and 10°C. The hydrochloride crystallizes. It is dried, washed in cold methylethylketone and is recrystallized in isopropanol. 61 g of crystals are obtained having a melting point of 194°C.

EXAMPLE VII

N-(1-PROPYL-2-PIPERIDYLMETHYL)-2-ALLYLOXY-4-METHYL-5-CHLOROBENZAMIDE HYDROCHLORIDE

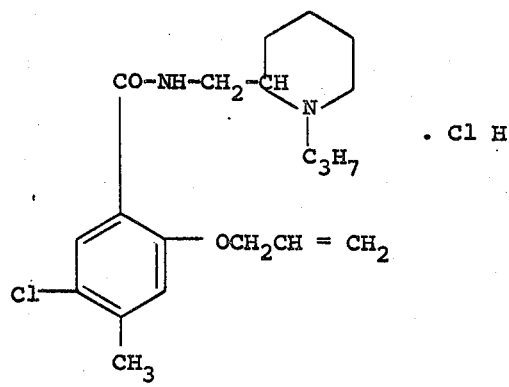

In a three-necked 100 ml flask, equipped with a mechanical agitator, an ascendant refrigerant and a thermometer, there are introduced 5 g of 2-allyloxy-4-methyl-5-chlorobenzoic acid and 3.2 ml of thionyl chloride. The mixture is heated on a water bath for 2 hours, and the excess thionyl chloride is removed under vacuum. The product is dissolved in 50 ml of methylethylketone and is introduced drop by drop into a solution of 3.45 g of 1-propyl-2-amino-methyl-piperidine in 25 ml of methylethylketone. After agitation for two hours at room temperature, the solvent is removed under vacuum. The residue is recovered with fresh methylethylketone and is allowed to crystallize after treatment with vegetable charcoal and is filtered. The crystals melt at 161°C. (Yield: 45% Weight: 4 g)

EXAMPLE VIII

N-(1-PROPYL-2-PYRROLIDYLMETHYL)-2-ETHOXY-4-HYDROXY-5-BROMOBENZAMIDE HYDROCHLORIDE

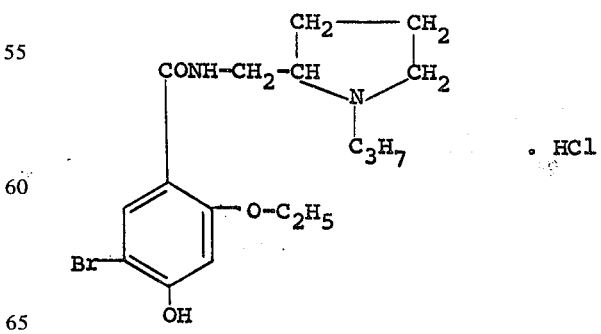

Into a 500 ml flask, surmounted on a Vigreux column, there are introduced 43 g of methyl 2-ethoxy-4-hydroxy-5-bromobenzoate dissolved in 120 ml of dry xylene and 44.3 g of 1-propyl-2-aminomethyl pyrrolidine. The methanol formed is slowly distilled at about 64°C, then a little of the xylene. The duration of the reaction is 3 hours. Then the remainder of the xylene and the excess amine are distilled under vacuum. The residue is recovered with 200 ml of water and 50 ml of hydrochloric acid (d=1.18) are added. The hydrochloride crystallizes when cooled. It is dried, washed with a small amount of ice water and dried at 50°C. About 58% (38 g) of N-(1-propyl-2-pyrrolidylmethyl)-2-ethoxy-4-hydroxy-5-bromobenzamide hydrochloride is obtained, having a melting point of 186°C.

If a N-(1-propyl-2-pyrrolidylmethyl)-2-ethoxy-4-hydroxy-5-halobenzamide having a different halogen in the 5 position is desired, the stoichiometric equivalent of the corresponding methyl 2-ethoxy-4-hydroxy-5-halobenzoate is employed instead of the 43 g of methyl 2-ethoxy-4-hydroxy-5-bromobenzamide as employed in this example. For instance, if the corresponding 5-fluoro or 5-iodo analog were desired, the stoichiometric equivalent of methyl 2-ethoxy-4-hydroxy-5-fluorobenzoate or the stoichiometric equivalent of methyl 2-ethoxy-4-hydroxy-5-iodobenzoate would be used.

The compositions of this invention have been studied pharmacologically and clinically to determine their non-toxicity and their anti-emetic activity.

The low toxicities studied in mice showed that the compositions of this invention have a toxicity entirely compatible with therapeutic use. The results of the studies made are given in the following table:

Vomitings ceased in 30 minutes after the injection of apomorphine.

The following calculations represent the experimental results for several of the compositions of this invention:

| COMPOSITIONS | Rate of protection of dose of 250 μg/Kg (base) |
|---|---|
| N-(1-ethyl-2-pyrrolidylmethyl)-2-methoxy-4-methyl-5-chlorobenzamide | 100 % |
| Racemic N-(1-ethyl-2-pyrrolidylmethyl)-2-methoxy-4-hydroxy-5-chlorobenzamide | 100 % |
| Dextro N-(1-ethyl-2-pyrrolidylmethyl)-2-methoxy-4-hydroxy-5-chlorobenzamide | 100 % |
| Levo N-(1-ethyl-2-pyrrolidylmethyl)-2-methoxy-4-hydroxy-5-chlorobenzamide | 100 % |

The experimental results were confirmed in the clinic where the products were administered in the form of tablets or ampoules of a pharmacologically acceptable salt.

Treatments given under clinical conditions corresponding to the pharmacodynamic showed no manifestation of medicament intolerance. Vomiting ceased quickly and did not reappear until treatment was stopped.

The anti-emetic compositions of this invention can be administered in the form of tablets, injectable ampoules or aerosols, suppositories, granulated saccharin or sweetened syrup.

What is claimed is:

1. A method of protection a mammal against emesis which comprises administering to said mammal an anti-emetic effective amount of a compound selected from the group consisting of a heterocyclic benzamide and its pharmaceutically acceptable acid addition salts and quaternary ammonium salts, said heterocyclic benzamide having the formula:

| COMPOSITIONS | DL$_{50}$ in mg/kg composition in base state | | | |
|---|---|---|---|---|
| | Per os | Intravenously | Intraperitoneally | Subcutaneously |
| N-(1-ethyl-2-pyrrolidylmethyl)-2-methoxy-4-methyl-5-chlorobenzamide | 302–322 | 29.5–28.6 | 102–107 | 201–204 |
| Racemic N-(1-ethyl-2-pyrrolidylmethyl)-2-methoxy-4-hydroxy-5-chlorobenzamide | 886–931 | 143–139 | 269–280 | 448–470 |
| Dextro N-(1-ethyl-2-pyrrolidylmethyl)-2-methoxy-4-hydroxy-5-chlorobenzamide | | 113–122 | | |
| Levo N-(1-ethyl-2-pyrrolidylmethyl)-2-methoxy-4-hydroxy-5-chlorobenzamide | | 140–144 | | |
| N-(1-ethyl-2-pyrrolidylmethyl)-2-methoxy-4-hydroxy-5-chlorobenzamide bromomethylate | | 60–61.5 | | |

The antiemetic action of these compositions on the vomiting centers was studied in the dog with the aid of apomorphine according to the technique of CHEN and ENSOR, together with DUCROT and P. DECOURT. Lots of 4 dogs were treated.

Apomorphine was administered subcutaneously in dosage of 0.10 mg/kg. The compositions tested were administered 30 minutes before, also subcutaneously.

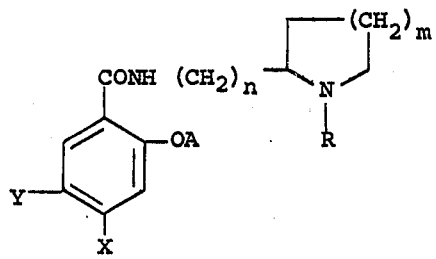

in which A is allyl or lower alkyl; R is allyl or lower alkyl; X is hydroxy; Y is halogen, $m$ is a whole number less than 3 and $n$ is a whole number less than 4.

2. The method of claim 1 in which R of said compound is ethyl and $m$ is 1.

3. The method of claim 1 in which said compound is a racemic form of N-(1-ethyl-2-pyrrolidylmethyl)-2-methoxy-4-hydroxy-5-chlorobenzamide.

4. The method of claim 1 in which said compound is in the levo or dextro form.

5. The method of claim 1 in which said compound is in the dextro form of N-(1-ethyl-2-pyrrolidylmethyl)-2-methoxy-4-hydroxy-5-chlorobenzamide.

6. The method of claim 1 in which said compound is the levo form of N-(1-ethyl-2-pyrrolidylmethyl)-2-methoxy-4-hydroxy-5-chlorobenzamide.

7. The method of claim 1 in which said compound is N-(1-ethyl-2-pyrrolidylmethyl)-2-methoxy-4-hydroxy-5-chlorobenzamide bromomethylate.

8. The method of claim 1 in which said compound is N-(1-propyl-2-pyrrolidylmethyl)-2-ethoxy-4-hydroxy-5-bromobenzamide hydrochloride.

* * * * *